United States Patent
Simola et al.

(10) Patent No.: US 9,642,554 B2
(45) Date of Patent: May 9, 2017

(54) METHOD FOR ADJUSTING INTERFERENCE SIGNAL SPACE IN BIOMAGNETIC FIELD MEASUREMENTS

(75) Inventors: Juha Simola, Helskini (FI); Samu Taulu, Helsinki (FI)

(73) Assignee: Elekta AB (publ), Stockholm (SE)

( * ) Notice: Subject to any disclaimer, the term of this patent is extended or adjusted under 35 U.S.C. 154(b) by 1015 days.

(21) Appl. No.: 13/808,578

(22) PCT Filed: Jul. 6, 2011

(86) PCT No.: PCT/FI2011/050639
§ 371 (c)(1),
(2), (4) Date: Jan. 4, 2013

(87) PCT Pub. No.: WO2012/004458
PCT Pub. Date: Jan. 12, 2012

(65) Prior Publication Data
US 2013/0109954 A1  May 2, 2013

(30) Foreign Application Priority Data
Jul. 6, 2010  (FI) ..................................... 20105769

(51) Int. Cl.
*A61B 5/00* (2006.01)
*A61B 5/05* (2006.01)
(Continued)

(52) U.S. Cl.
CPC ............... *A61B 5/05* (2013.01); *A61B 5/0042* (2013.01); *A61B 5/04008* (2013.01);
(Continued)

(58) Field of Classification Search
CPC .................................................. G01R 33/025
See application file for complete search history.

(56) References Cited

U.S. PATENT DOCUMENTS 5,136,242 A  8/1992  Abraham-Fuchs
5,187,436 A  2/1993  Mallick
(Continued)

FOREIGN PATENT DOCUMENTS

EP  0982597 A2  3/2000
FI  115324 B1  4/2005
(Continued)

OTHER PUBLICATIONS

A. Ziehe et al,; "A comparison of ICA-based artifact reduction methods for MEG" Recent Advances in Biomagnetism: Proceedings of the 12th International Conference on Biomagnetism, Helsinki University of Technology; 2001, pp. 895-898.
(Continued)

*Primary Examiner* — Joseph M Santos Rodriguez
(74) *Attorney, Agent, or Firm* — Studebaker & Brackett PC (57) ABSTRACT

The present invention introduces a method for adjusting interference signal estimates provided by multichannel biomagnetic field measurements. A so-called Signal Space Separation method (SSS) is applied in the calculatory analysis of the measurement signals, providing for the division of the sources causing the fields in objects of interest and external interferences. When the signal basis representing the interferences has been estimated, this interference signal estimate is adjusted by measuring the fields without the object to be measured and without changing the sensor assembly. Interference components obtained in this manner are analyzed in such a way as to include only the most significant interference components. An adjusted interference subspace is formed, by means of which signal processing and the analysis of the useful signals can be continued.

15 Claims, 8 Drawing Sheets

(51) Int. Cl.
   *A61B 5/04* (2006.01)
   *G01R 33/025* (2006.01)
   *G01R 33/035* (2006.01)
(52) U.S. Cl.
   CPC .......... *A61B 5/4064* (2013.01); *A61B 5/7225* (2013.01); *G01R 33/025* (2013.01); *G01R 33/035* (2013.01)

(56) References Cited

U.S. PATENT DOCUMENTS

| | | | |
|---|---|---|---|
| 6,538,436 B1 | 3/2003 | Simola et al. | |
| 7,463,024 B2 | 12/2008 | Simola et al. | |
| 2008/0294386 A1* | 11/2008 | Taulu | G01R 33/025 702/191 |

FOREIGN PATENT DOCUMENTS

| | | | | |
|---|---|---|---|---|
| FI | WO 2005078467 A1 * | 8/2005 | ........... | G01R 33/025 |
| WO | 2004/081595 A1 | 9/2004 | | |

OTHER PUBLICATIONS

M.A. Uusitalo et al.; "Signal-space projection method for separating MEG or EEG info components"; Medical and Biological Engineering and Computing; vol. 35, No. 2, pp. 135-140, Mar. 1997, DOI; 1007/BF02534144.

S. Taulu et al.; "The Signal Space Separation Method"; Arxiv.org. preprint library, arXiv: physics/040116; Jan. 30, 2004; Internet-osoitteesta: http://arxiv.org/abs/physics/040116.

Finnish Search Report; 20105769; Mar. 2, 2011.

International Preliminary Report on Patentability; PCT/FI2011/050639; Aug. 31, 2012.

International Search Report; PCT/FI2011/050639; Oct. 28, 2011.

T.E. Ozkurt; "Decomposition of Magnetoencephalographic Data into Components Corresponding to Deep and Superficial Sources"; IEEE Transactions on Biomedical Engineering; vol. 55, Issue 6 pp. 1716-1727; ISSN 0018-9294. DOI: 10.1109/TBME.2008.919120.

\* cited by examiner

METHOD FOR ADJUSTING INTERFERENCE SIGNAL SPACE IN BIOMAGNETIC FIELD MEASUREMENTS

FIELD OF THE INVENTION

The invention relates to magnetic imaging methods in multichannel measurement devices applying such methods, and particularly to the improvement of the accuracy of such multichannel measurement methods.

BACKGROUND OF THE INVENTION

Particularly in medical research, various imaging methods are used in the analysis of tissue structures and brain signals. Methods used in different applications include magnetic resonance imaging (MRI), simply referred to as magnetic imaging, which is applicable to different parts of the body, and magnetoencephalographic imaging (MEG), which means the measurement and analysis of magnetic fields generated by the electric activity of the brain.

It is typical of the imaging methods that a large set of measurement channels and related measurement sensors are needed therein. The sensors must be very low-noise and situated close to the object to be measured. The typical noise level of a measurement sensor measuring a magnetic field is of the order of a few femtoteslas. It is characteristic of a measurement situation that the flux densities to be measured are very low (for example of the order of 10 . . . 1000 fT), and the external interference fields prevailing in the measurement situation may be quite large in comparison to the flux densities, even of the order of 1 . . . 10 µT. The estimation of the portion of different interference signals in the overall measurement signal and the elimination of the effect of interferences from measurement results is thus extremely essential in multichannel biomagnetic measurement methods.

In the prior art, interferences have been compensated for by using for example a so-called reference sensor assembly at a slight distance from the actual set of measurement sensors. Such reference sensors measure a signal that exhibits only the portion of external interference and practically not at all the useful signal originating from the human body to be measured. Then the interference signal can simply be reduced or projected off from the signal measured by the actual assembly. The problem with the reference sensor method is that the interferences are measured from a site different from the actual biomagnetic signals. If the interference field is not uniform, there is a need to extrapolate the interference field data in such a way as to obtain as good an estimate as possible specifically in the area of the set of measurement sensors.

Another known method is to use a compensating set of coils located in the vicinity of a measurement site to generate a magnetic field compensating for interferences in the area of the set of measurement sensors on the basis of measured interference field information. The problem in this method is to generate the compensating field in such a way that the interference appearing in the area of each measurement sensor can be sensor-specifically canceled even in the case of a non-homogeneous interference field.

A third prior art method is to locate the measurement sensors within a magnetically shielded room (MSR), whereby interferences originating from the environment can be significantly damped. The shielded room typically consists of many superposed metal layers (for example aluminum or suitable metal alloy can be used) constructed in such a way that the interference signals are damped substantially over a large frequency band in such a structure. The shielded room can be fixedly built in a desired site, which is quite an expensive solution, or it may be structurally lighter and built from elements in a desired space and is later moveable to a new site, if necessary. The problem of shielded rooms in minimizing the effects of interferences is that the walls of the shielded room itself may contain magnetic materials and thus they may act as an independent source of magnetic interference signals. A light shielded room is additionally susceptible to vibration, which may further generate an additional magnetic source. Perhaps the most important restriction of shielded rooms, however, is that they do not damp interferences generated within the room. This is a significant problem particularly in clinical MEG studies.

A calculatory method used in the analysis of measured signals is the so-called Signal Space Separation method (SSS method), which is discussed for example in patent publication FI 115324. The SSS method is currently quite amply used in the art. It is a calculatory method for separating multichannel measurement signal information, on the basis of the locations of the sources, into various signal bases, i.e. subspaces that are linearly independent of one another. The SSS is purely based on the geometry of the sensor assembly and natural laws. The calculation according to the principle of the SSS is begun by Maxwell's equations representing the relations of electric and magnetic fields. In the SSS method, it is possible to separate the magnetic fields generated by the useful sources (such as the brain) and the magnetic fields originating from external interference sources. In other words, series developments are calculated in the SSS method using division according to sources located in different sites. It may be referred to as a source modeling method for the multichannel measurement signal in a volume where the magnetic fields to be determined are irrotational and sourceless. The SSS method does not need advance information about the types or locations of the different signal sources but functions correctly in the cases of different types of signal sources, also when examined as a function of time even when the location and/or intensity of the sources changes. In the calculation according to the SSS method, the geometry of the sensor assembly thus plays an important role. Associated to the geometry is also the fact that, in addition to the location, the position of the sensors significantly affects the measured signal because the magnetic field is a direction-dependent quantity. Calibration of the sensors in this context means that the calculation logic has sufficiently accurate information about the locations and positions of the sensors, i.e. the difference between an estimate used in the calculation and the actual real-world situation is determined as accurately as possible. When the calibration information has been determined, it can be observed in the calculation to obtain more accurate information about the useful signals and, furthermore, more accurate analysis results on the basis thereof. As for the SSS method, it can be stated that a calculated subspace formed by the interferences is produced therein on the basis of the measurement results and, on the basis of this information, the desired biomagnetic signal is more accurately accessed.

The shielding factor of a method or device means the extent to which external interferences can be damped by a desired method or device. With default settings of a typical MEG device, a shielding factor of the order of approximately 20 is reached with the SSS method, i.e. using a MEG device that applies the calculation algorithm of the SSS method, the external interferences can be damped to approximately $\frac{1}{20}$ compared with what they would be without the SSS method. After so-called fine calibration, the shielding factor of the SSS method typically increases to a value of 100 . . . 150.

Advantages of the SSS method include that it observes all interferences regardless of time and place. Since the calculation is made independently for each sample, it observes the changing situations regardless of whether the interference sources are changing inside or outside the measurement area, i.e. the shielded room. A problem of the SSS method is that it is sensitive to the above-mentioned calibration errors, i.e., for example, a signal deviation measured by one of the sensors may not be due to interference but a small unrecognized deviation in the position of the sensor.

SSP method, in turn, means a so-called projection method ("Signal Space Projection"), based on projecting off the observed interference subspaces, i.e. components, by removing that dimension in question from the measured signal. The principle of the SSP method has been described, for example, in Uusitalo, Ilmoniemi: "Signal-space projection method for separating MEG or EEG into components", Medical & Biological Engineering & Computing 135-140, 1997. Interference signals can typically be measured in a situation where the object to be measured is excluded from the space to be measured, i.e. by setting the MEG device to measure without a patient inside the device. In this case, magnetic interference fields exclusively originating from the environment can be measured by the sensors of the device at the moment of that particular examination. After this, expressed in a simplified manner, the most essential interference component(s) (conceivable as a vector) is determined from the measured interference signal and the signal measured in a situation including the useful measurement object is projected after this determination in an orthogonal direction relative to said interference. In this case, the most essential forms of interference can be removed from the actually measured overall signal. A weakness of the SSP method is that part of the useful signal under examination is also projected off, unless it is fully orthogonal to the orientation of the main interference. Another weakness of the projection method is that it is not able to observe timedependent changes in an interference field because the interference subspace is only determined according to the situation of a specific period. In this case, interference sources changing in time are not correctly observed when the measurement is later renewed. An advantage of the SSP is that the calibration errors due to the placement and positions of the sensors can be taken into account by this method.

The main problem of the prior art is that magnetic interference fields caused by external interference sources can be damped only approximately to the 100th part. Even when damped, the magnitudes of interference fields are significantly large compared with the typical biomagnetic fields to be measured. Thus, there still exists a need to damp the effect of external interferences in biomagnetic multichannel measurements in one way or another.

As already stated above, the use of a so-called light shielded room around the measurement apparatus also entails problems. In addition to the possibility that the shielded room itself contains magnetic materials, a lightweight shielded room may also tremble, which may constitute a new magnetic interference source.

OBJECTIVE OF THE INVENTION

The objective of the invention is to disclose a new type of a method for efficiently eliminating the effect of external interference sources in measurements made by multichannel measurement devices such as the measurements particularly made by MEG and MRI imaging devices. A further objective of the invention is to remedy the above-mentioned problems.

SUMMARY OF THE INVENTION

The present invention introduces a method for adjusting field components included in a magnetic field measured by a multichannel measurement device, wherein the measurement device comprises a set of measurement sensors and a data processing logic. In the method, two calculated signal subspaces are first generated by means of a SSS method, wherein the first calculated signal subspace represents the vectors of the signal components in a linearly independent signal basis of the useful signal, and the second calculated signal subspace represents the vectors of the signal components in a linearly independent signal basis of interference signals.

The method is further characterized in that the multichannel magnetic field of interference signals is measured therein without the useful signal source, the most intensive forms of interference signals due to interferences and/or incorrectly functioning signal channels are determined from the magnetic field of interference signals, said second calculated signal subspace is adjusted by adding the most intensive forms of interference signals thereto, and the useful signal is determined by continuing the use of the SSS method with the adjusted signal subspace.

In one embodiment of the present invention, included in the forms of the most intensive interference signals are those measured magnetic field components of interference signals wherein the signal intensity related to vectors representing such components exceeds a desired threshold value.

In one embodiment of the present invention, at least one of the measured components of the subspace of interference signals is added to the components of the second calculated signal subspace, and the components of the thus supplemented second signal subspace are combined in such a way that the components of the adjusted signal subspace being generated together form a linearly independent basis.

In one embodiment of the present invention, the combination is made by calculating the singular value decomposition for the components of the signal subspace under examination.

In one embodiment of the present invention, the signal of an incorrectly functioning signal channel is divided in such a way as to include the correctly appearing signal component and the incorrect signal component deviating from other channels, and only the incorrect signal component is included in the measured subspace of interference signals from said signal channel.

In one embodiment of the present invention, the calculated signal subspaces are respanned after at least one incorrectly functioning signal channel has been included in the measured subspace of interference signals.

In one embodiment of the present invention, an adjustment to the first calculated signal subspace generated on the basis of the conducted magnetic field measurements is determined in a manner corresponding to the second calculated signal subspace.

According to a second aspect of the present invention, the inventive idea comprises a multichannel measurement device arranged to measure a magnetic field and adjust the field components included therein. The measurement device comprises a set of measurement sensors and a data processing logic arranged to generate two calculated signal subspaces by means of the SSS method, wherein the first calculated signal subspace represents the vectors of signal components in a linearly independent signal basis of the useful signal, and the second calculated signal subspace represents the vectors of signal components in a linearly independent signal basis of interference signals.

The measurement device is further characterized by being arranged to measure the multichannel magnetic field of the interference signals without the useful signal source, and the data processing logic is further arranged to determine the most intensive forms of the interference signals due to interferences and/or incorrectly functioning signal channels from the magnetic field of the interference signals, adjust said second calculated signal subspace by adding the most intensive forms of the interference signals therein, and determine the useful signal by continuing the use of the SSS method with the adjusted signal subspace.

In one embodiment of the present invention, the data processing logic is further arranged to include in the forms of the most intensive interference signals those measured magnetic field components of interference signals wherein the signal intensity related to vectors representing such components exceeds a desired threshold value.

In one embodiment of the present invention, the data processing logic is further arranged to add at least one of the measured components of the subspace of interference signals to the components of the second calculated signal subspace and combine the components of the thus supplemented second signal subspace in such a way that the components of the adjusted signal subspace being generated together form a linearly independent basis.

In one embodiment of the present invention, the data processing logic is further arranged to make the combination by calculating the singular value decomposition for the components of the signal subspace under examination.

In one embodiment of the present invention, the data processing logic is further arranged to divide the signal of an incorrectly functioning signal channel in such a way as to include the correctly appearing signal component and the incorrect signal component deviating from other channels, and to include only the incorrect signal component in the measured subspace of interference signals from said signal channel.

In one embodiment of the present invention, the data processing logic is further arranged to respan the calculated signal subspaces after at least one incorrectly functioning signal channel has been included in the measured subspace of interference signals.

In one embodiment of the present invention, the data processing logic is further arranged to determine an adjustment to the first calculated signal subspace generated on the basis of the conducted magnetic field measurements in a manner corresponding to the second calculated signal subspace.

According to a third aspect of the present invention, the inventive idea further comprises a computer program for adjusting field components included in a magnetic field measured by a multichannel measurement device, wherein the measurement device comprises a set of measurement sensors and a data processing logic. The computer program comprises program code which, when run on the data processing logic, has been arranged to execute the step of:

generating two calculated signal subspaces by means of the SSS method, wherein the first calculated signal subspace represents the vectors of signal components in a linearly independent signal basis of the useful signal, and the second calculated signal subspace represents the vectors of signal components in a linearly independent signal basis of interference signals.

As characteristic features, the computer program is further arranged to execute the steps of:

measuring the multichannel magnetic field of the interference signals without the useful signal source;

determining the most intensive forms of the interference signals due to interferences and/or incorrectly functioning signal channels from the magnetic field of the interference signals;

adjusting said second calculated signal subspace by adding the most intensive forms of the interference signals therein; and determining the useful signal by continuing the use of the SSS method with the adjusted signal subspace.

In one embodiment of the present invention, the computer program is stored on a data processing logic readable medium.

One of the most important advantages of the present invention is that the shielding factor of the SSS method generally used in the MEG measurements can be improved by the invention from the typical 150 of the optimized default settings even up to a value of approximately 1000. This is an important additional damping in the elimination of external interferences and is emphasized particularly in situations where the interference is very high intensity. In practice, the effect of the invention can be compared to making the shielded room surrounding the MEG measurement arrangement as if thicker by intensifying the measurement and calculation algorithm, but also stabilized in such a way as to tremble less. A further advantage is that a good accuracy in the measurement results of the useful signal is achieved by the method over a wide frequency band, for example a measurement band of 0 to 2 kHz that is generally used in practice, and in this connection an accuracy of approximately 1 per mil, up to the high frequencies, can be reached. In practicing the invention, there is no need difficultly to calibrate for example 306 channels, but the method of the present invention performs the elimination of calibration errors in a simple and efficient manner. Another advantage of the invention is that the good properties of the SSS method are combined therein with the advantageous features of projection methods in a new unparalleled manner.

DETAILED DESCRIPTION OF THE INVENTION

The purpose of the present invention is to introduce adjusting steps for measurement methods conducted by multichannel measurement devices more specifically to determine the subspace caused by interferences appearing in the measurement results, and thereby to determine the interesting useful signal distinctly more accurately than before.

The basis of the principle of the invention is Signal Space Separation, i.e. the SSS method, introduced in the prior art and summarized above. The quantity to be measured in one typical example is the magnetic field, i.e. the application of use in this case is a magnetoencephalographic, i.e. MEG, device. In the SSS method, the central idea is that by utilizing Maxwell's equations and information about the geometry of the sensor assembly, it is possible to calculate a result indicating which part of the measured signal is interesting biomagnetic signal originating from inside the measurement sensors and which part is external interferences originating from outside the sensors. In other words, the magnetic multipole moments, i.e. the weights of signal components, in a linearly independent signal basis of the useful signal and, in turn, in a signal basis formed by interference signals, can be calculated as a result. Being a realtime method, the SSS adapts to the current prevailing interference situation, i.e. the SSS always measures the real prevailing magnetic field, regardless of the changes of the signal sources inside or outside the volume to be measured that might occur in time. The results provided by the SSS are, however, affected by the above-mentioned calibration error, i.e. the inaccuracy in the sensitivity, location and positions of the measurement sensors (the supposed location and position information compared with the real location and position information) directly affects the results provided by the SSS method.

In one embodiment of the present invention, the measured multichannel signal is first processed by calculating with the SSS method as has been done in the prior art. The processing is conducted to a point where the signal subspace formed by interferences is determined in the calculation. The present invention now engages in fine-tuning this estimated interference space in such a way as to correspond to the real prevailing interference space with even much better an accuracy than has been possible in the prior art. It can be figuratively said that the "vector" representing an interference subspace is changed a little as for the direction thereof. In other words, it can be said that a new interference component is added to the calculated interference subspace, whereby the new interference subspace expressed as the sum will correspond to the real prevailing interference field information significantly better than before. To express that in yet another way, it can be stated that the interference model obtained by the prior art methods is defective in that it lacks a certain form or forms of interference which, nevertheless, exists in the reality. The present invention aims at improving this interference model in this respect.

Assume in the following example that we have a 306-channel set of signals, i.e. the MEG device to be used has 306 measurement channels. In operating by the SSS method, the field components are calculated from the measurement results up to a desired order.

The field components can be separated according to the location of the source of the magnetic field causing each component. The source may be inside the sensor assembly (brain signals) or significantly outside the assembly (external interference sources).

In one embodiment of the prior art, it is additionally possible to separate the interference sources situated in a so-called intermediate space between the above-mentioned volumes, whereby the non-interesting sources situated very close to the set of measurement sensors are included in the examination. This so-called intermediate space embodiment is described in published patent application FI 20050445.

In operating with the SSS method it is assumed that the measurement sensors are situated in a volume not including any magnetic sources. In practice, the distance of the sensors from the nearest signal source is of the order of at least 2 to 4 cm, whereby the magnetic field measured by the set of sensors and the gradients thereof up to a desired order behave sufficiently neatly, i.e. abrupt local changes do not occur therein. In other words, the orders denote the degrees of freedom of the biomagnetic field and can be determined up to the order by which the amplitude exceeds the noise level of the sensors.

In the following, the origin is assumed to the center of the area formed by the measurement sensors, i.e. to the center of the head in the measurement of brain signals. The measurement volume can be examined by means of concentric spherical shells, the radii of which are suitably selected. The division can be made for example in such a way that all useful magnetic sources, i.e. in the case of the MEG measurement the head of the patient under examination, are situated within the inmost spherical shell. Next, the sensors of the measurement device itself are located in the layer outside the inmost spherical shell, additionally taking care that magnetic sources are not found in this layer. Situated in a third volume outside this layer, which may principally be defined as extending up to infinity, are all sources of external magnetic interferences.

The potential related to a field can be solved as a solution to Laplace's equation applying so-called spherical harmonics. The potential can be formed as the sum of two series developments in such a way that the first series development diverges at the origin and the second series development diverges at the infinity. This means that the first series development characterizes the magnetic sources which are biomagnetic sources within the sensor assembly, and the second development characterizes external interference sources situated in the outmost, or the third, volume.

After this, the measured magnetic field is expressed by signal vectors in such a way that the measured overall signal is the sum of two linear combinations, wherein both linear combinations are presented by suitable basis vectors. In mathematical terms:

$$\phi = \sum_{l=1}^{L_{in}} \sum_{m=-l}^{l} \alpha_{lm} a_{lm} + \sum_{l=1}^{L_{out}} \sum_{m=-l}^{l} \beta_{lm} b_{lm} \qquad (1)$$

which gives, in a matrix form:

$$\Phi = \overline{S}x = [\overline{S}_{in} \overline{S}_{out}] \cdot \begin{bmatrix} x_{in} \\ x_{out} \end{bmatrix}, \text{ wherein} \qquad (2)$$

$$\bar{S}_{in} = [\bar{a}_{1,-1} \dots \bar{a}_{LinLin}] \quad (3)$$

$$\bar{S}_{out} = [\bar{b}_{1,-1} \dots \bar{b}_{LoutLout}] \quad (4)$$

$$\bar{x}_{in} = [\alpha_{1,-1} \dots \alpha_{LinLin}]^T \quad (5)$$

$$\bar{x}_{out} = [\beta_{1,-1} \dots \beta_{LoutLout}]^T \quad (6)$$

In the above notation, $S_{in}$ represents the set of basis vectors representing biomagnetic signals, and $S_{out}$ represents, respectively, the set of basis vectors representing interference signals. Notations $x_{in}$ and $x_{out}$ denote so-called multipole moments which practically mean the weighting coefficient of each S to provide the field vector $\Phi$. The dimension of the SSS basis, i.e. the number of basis vectors, can be determined in the following way:

$$n = (L_{in}+1)^2 + (L_{out}+1)^2 - 2 \quad (7)$$

For example, values $L_{in}=8$ and $L_{out}=3$ give n=95. When N>n (N being the number of channels), a linearly independent SSS basis is obtained, covering all measurable magnetic signals in a desired volume. The separation result into the useful signal basis and interference signal basis is unambiguous and as a result gives the estimated useful signal:

$$\hat{x} = \begin{bmatrix} \hat{x}_{in} \\ \hat{x}_{out} \end{bmatrix} = S^{PI}\Phi, \quad (8)$$

wherein PI means the pseudoinverse of S, i.e. in mathematical terms $S^{PI} = (S^T S)^{-1} S^T$.

The accuracy of $\hat{x}$ depends on the condition number of S and calibration accuracy of the set of sensors because the SSS method is based on direct information about the geometry of the sensor assembly. After this, the signals corresponding to the biomagnetic and interference sources can be reconstructed in the following manner:

$$\hat{\phi}_{in} = \bar{S}_{in} \hat{x}_{in} \text{ and} \quad (9)$$

$$\hat{\phi}_{out} = \bar{S}_{out} \hat{x}_{out} \quad (10)$$

wherein $\hat{\phi}_{in}$ and $\hat{\phi}_{out}$ are the field vectors caused by the object to be measured or by external interferences, respectively, each S represents basis vectors or subspaces, and each x is a multipole moment, i.e. practically a weighting coefficient for different basis vectors.

Next, the field portion $\hat{\phi}_{out}$ formed by interferences and estimated by the SSS method is taken under examination. Previously, this interference space has just been excluded from the overall signal, assuming that the calibration of the sensor assembly is perfect, i.e. accurate information about the location and position of each sensor is available. Since calibration errors always exist in the reality, we have the possibility of fine-tuning $\hat{\phi}_{out}$ better to correspond to the reality.

When we thus have the calculated interference subspace according to equation (10), this estimated interference subspace can be adjusted in one embodiment of the invention as follows. If, for the purpose of simplicity, we have for example 15 calculated, 306-dimensional vectors ($b_{lm}$), we can add, in this step, for example 5 306-dimensional vectors to the interference subspace, whereby the new summed basis represents a fine-tuned interference subspace. It can be said that each of these five vectors represents a "small deviation" to be added to the interference subspace. In principle, a similar adjustment can also be made to the basis vectors inside the sensor assembly, though the adjustment of the interference subspace is in practice a more important procedure because the interference signals are typically much more intensive than the useful signals.

The interference vectors, i.e. small deviations, to be added can be determined for example from the measured signal in a manner similar to the procedure of the projection methods. In other words, the most intensive interference forms not present in the calculated interference model as determined by the SSS because of calibration errors or some other reason are determined from the measured signal. This measurement is made without the actual object to be measured, i.e. for example the MEG measurement can be performed when the patient is not present in the magnetically shielded room. This way, the so-called interference subspace included in empty room can be accurately measured. In practice, a set of vectors is obtained, wherefrom those differing significantly from the norm of zero are picked. This step can be conducted for example by calculating the singular value decomposition which is a mathematical operation known per se.

As another type of an example of the above-mentioned interference vector to be added, the determination of the error signals of inoperative channels and elimination of the effect thereof can be mentioned. Such error signals can be added to the interference basis simply as 306-dimensional vectors, wherein the known poor channel has the value of 1 and the other channels have the value of 0. In this case, the error signal proper to the poor channel and independent of the other channels is modeled by the added vector in question, and the other channels will not have any signal bias whatsoever. This operation also has the advantage that a correct signal portion possibly provided by the poor channel is not lost.

Furthermore, it is important that the summed basis of interference vectors does not have any redundant vectors, i.e. for example two of the same vectors or two interference component vectors linearly dependent on one another. If linearly dependent vectors were included, further calculation would be unstable, i.e. the solution would not be unambiguous or could not be found at all. In this step, the combination of the calculated interference basis and measured interference basis is thus processed further in such a way that the summed set of interference vectors forms a linearly independent basis. At the same time, the number of interference vectors can typically be reduced so as to have the number thereof between the number of the vectors of the SSS interference basis and the number of the vectors of the interference basis extended with the projection method.

To specify the number of vectors it can be stated as an example that for instance 10 306-dimensional interference vectors can be produced by the SSS calculation. After this, for instance 5 interference vectors substantially deviating from zero are determined by the projection method. Then, it is observed that two of these vectors are redundant with two interference vectors of the SSS basis. As the final result, an interference vector matrix having the size of 306*13 is obtained, distinctively better corresponding to the real prevailing interference space than what has been previously possible to determine by any prior art method.

Figure 1A:
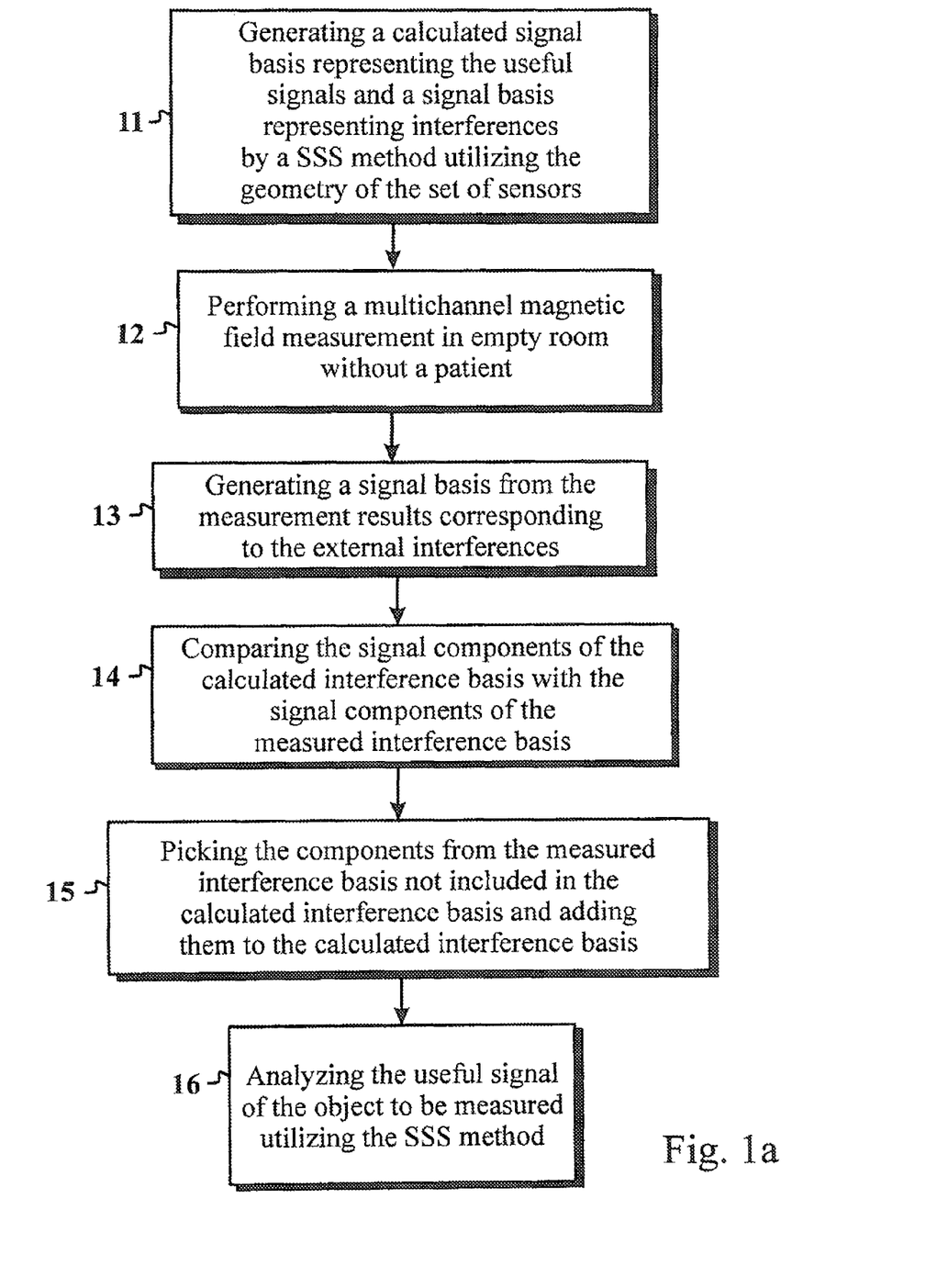
FIG. 1a shows an example of the method according to the invention in the form of a flow chart.

FIG. 1a shows one example of the steps of the method according to the present invention as a simplified flow chart. The measurement device for magnetic fields to be used is thus for example a MEG measurement apparatus located inside a magnetically shielded room, with a large set of measuring sensors, i.e. measuring channels, connected thereto. First, a calculatory analysis 11 based on the geometry (locations and positions) of the set of measurement sensors and natural laws (Maxwell's equations for electric and magnetic fields) is made, corresponding to the above-described prior art Signal Space Separation method (the SSS method). As the result of this step, calculated basis vector sets are obtained for the signal sources inside the set of sensors and interference sources outside the set of sensors. In other words, the field components representing the magnetic field to be later measured can be divided in this manner in two parts, i.e. series developments, one of which includes only the magnetic fields developed from the sources of volume inside the set of sensors, and the other one of which includes the interference field components originating from outside the set of sensors. These field components can be expressed by the calculated useful signal basis and by the calculated interference signal basis.

After this, a multichannel magnetic field measurement is performed without the presence of a patient, i.e. the object to be measured, 12, to determine the so-called magnetic field included by empty room. This way, the general interference space, i.e. the effect of all other signal sources except for the brain signals of the patient, is determined by measuring the magnetic fields in the area of the set of measurement sensors. By the measurement, a signal basis corresponding to external interferences can thus be generated from the measurement results 13. After this, A N-length interference vectors obtained by the SSS method 11 and B N-length interference vectors obtained by the measurement of empty room 12 can be separated for examination. Firstly, the norms of the vectors (geometrically the length, i.e. the amplitude of the signal component in an extended sense) are examined from the B interference vectors, and only those interference vectors are selected for further processing wherein the norm exceeds a desired threshold value. This way, only those components are selected which substantially deviate from zero, i.e. the components of the interference subspace most significantly affecting the measurements. After this screening, the essential components of the interference basis B are compared with the vectors 14 of the interference basis A. This is made by examining linear dependences between the pairs of vectors and, if found, such vectors are summed together and the redundant vectors are removed from the interference basis. By processing in the above manner, the number of interference vectors can be reduced, yet the information content contained by the set of interference vectors is not reduced.

From the above-mentioned comparison, a subset of the measured interference basis originally containing a number of B, i.e. C linearly independent components of the interference subspace, is obtained as a result, which can be added as a supplement to the calculated set of interference vectors containing a number of A 15. This way, an interference space distinctly better corresponding to the reality, a matrix having a size (N, A+C) by the above-mentioned notation, is obtained. After this, the analysis of the magnetic field measurements can be continued as desired 16. This can be made for example by continuing the use of the SSS method as in the prior art in such a way that accurate signal information representing the biomagnetic field is finally obtained as the end result. This can be further continued to perform the source modeling in such a way as to obtain accurate information about those locations of the brain where each field component was developed. Finally, a diagnosis concerning the condition of the patient can at best be determined from the location and intensity information of the brain signals by a specialist.

Figure 1B:
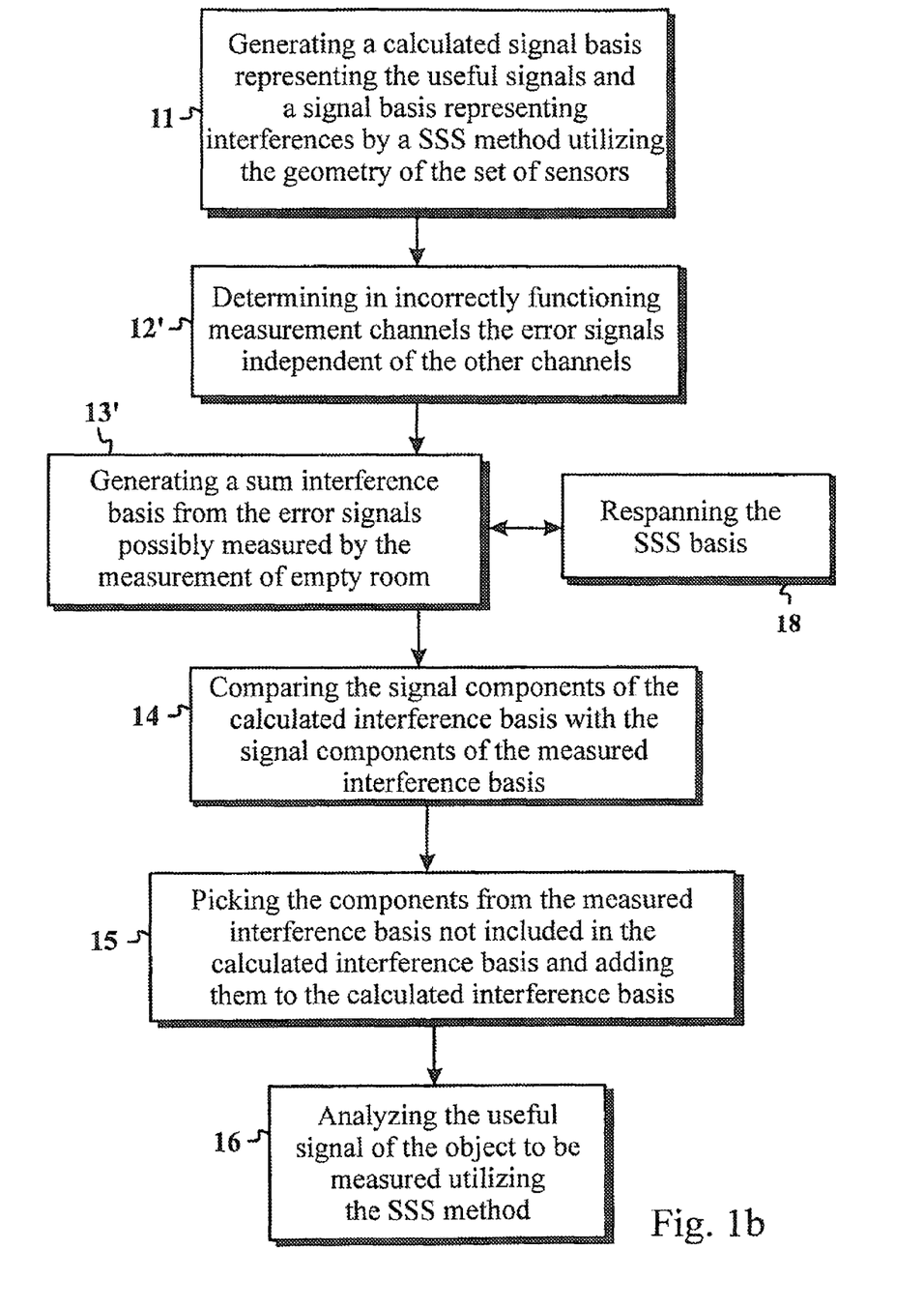
FIG. 1b shows a second example of the method according to the invention in the form of a flow chart.

FIG. 1b, in turn, shows a second example of the present invention in the form of a flow chart. In this example, the first step 11 is identical to the example of FIG. 1a. After this, the idea of the invention is used, however, to determine other types of interferences than above, namely the individual channels which, for one reason or another, contain an interference signal independent of the other channels or which are otherwise out of order. Such channels and the incorrect interference components expressed thereby are herein determined in step 12'. After this, the so-called measurement of empty room can also be made as described above in step 12 of FIG. 1a. When the error signals actually appearing in the measurement channels and the measured external interference signals are combined, a sum interference basis can be generated 13'. After this step, it is preferred to respan the basis vectors of the SSS signal subspaces 18. Then, it is possible to continue as in FIG. 1a, steps 14 to 16. In this processing, the errors contained by poor individual measurement channels can be removed from examination as in the case of external interferences.

Figure 1C:
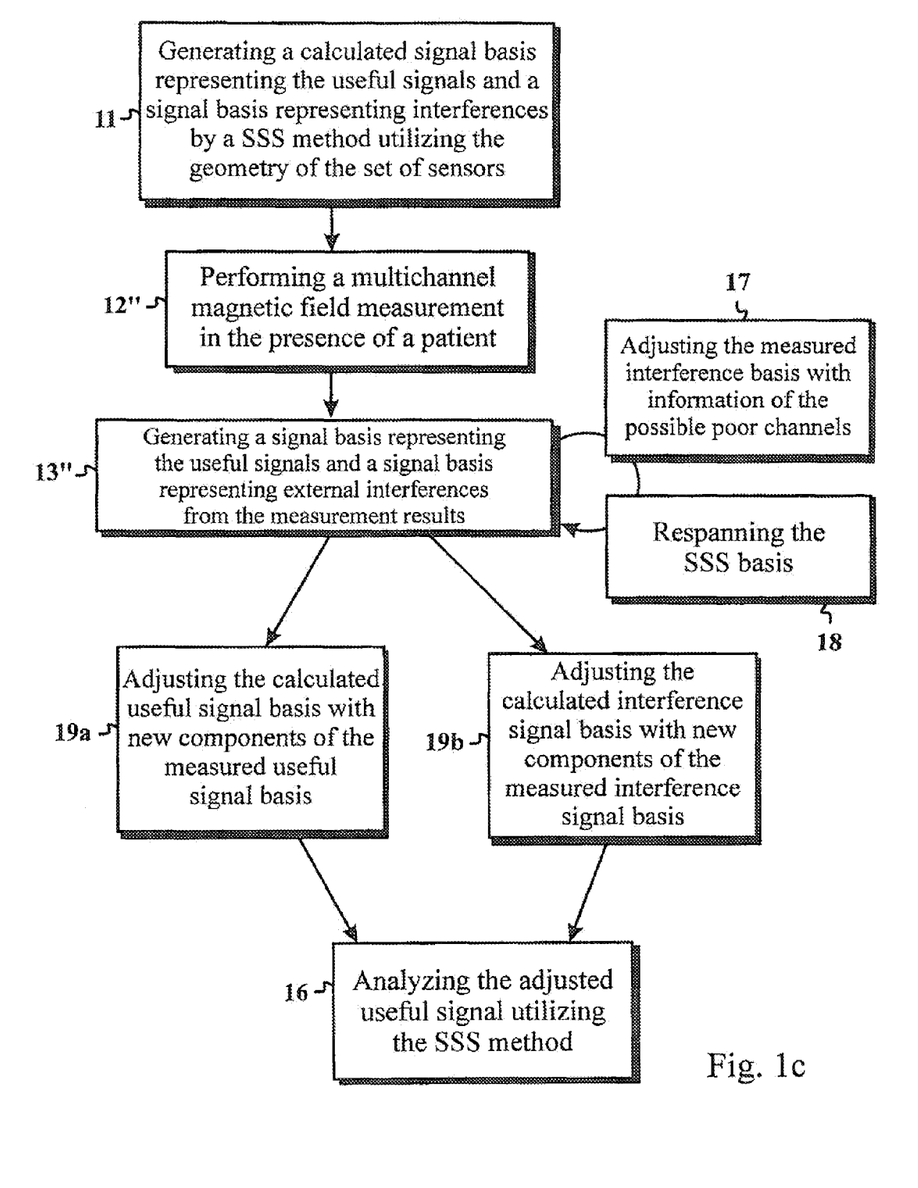
FIG. 1c shows a third example of the method according to the invention in the form of a flow chart.

FIG. 1c in turn shows a third example of the invention, also including the adjustment of the signal basis inside the set of sensors in addition to the adjustment of the interference basis. In this example, the first step 11 is identical to the preceding embodiments, i.e. two different signal bases are first generated by the SSS method. After this, the actual measurement can be performed, as the set of sensors of the measurement device is surrounding the head of a patient 12". Now, the information about magnetic fields is obtained based on real clinical measurement, part of the magnetic fields being external interferences and part of them being a biomagnetic signal originating from the brain, the amplitude of which may be of the order of several decades smaller than that of the interferences. In step 13", the measured signal can be split into a signal basis comprising the useful signal and a signal basis comprising the rest, i.e. the external interferences. After this, the additions according to FIG. 1b can be made on the measured interference space, i.e. the information of the poor channels, or the interference components contained by incorrectly operating channels, can be included 17 (this step is basically the same as 12' in FIG. 1b). After this step, it is preferred to respan the vectors of the SSS signal bases 18 as in the example of FIG. 1b.

Now we have both the measured components of the internal and external basis 13" as well as the calculated components of the internal and external basis 11. Correspondingly to the procedure of the previous examples in steps 14 to 15, the adjustment is now made in the useful signal basis 19a and the interference basis 19b both or just one of them. This way, the internal and external basis of the set of sensors can be, if necessary, both adjusted in such a way as better to correspond to the reality. Finally, the analysis of the signals can be continued 16 as above.

Figure 2A:
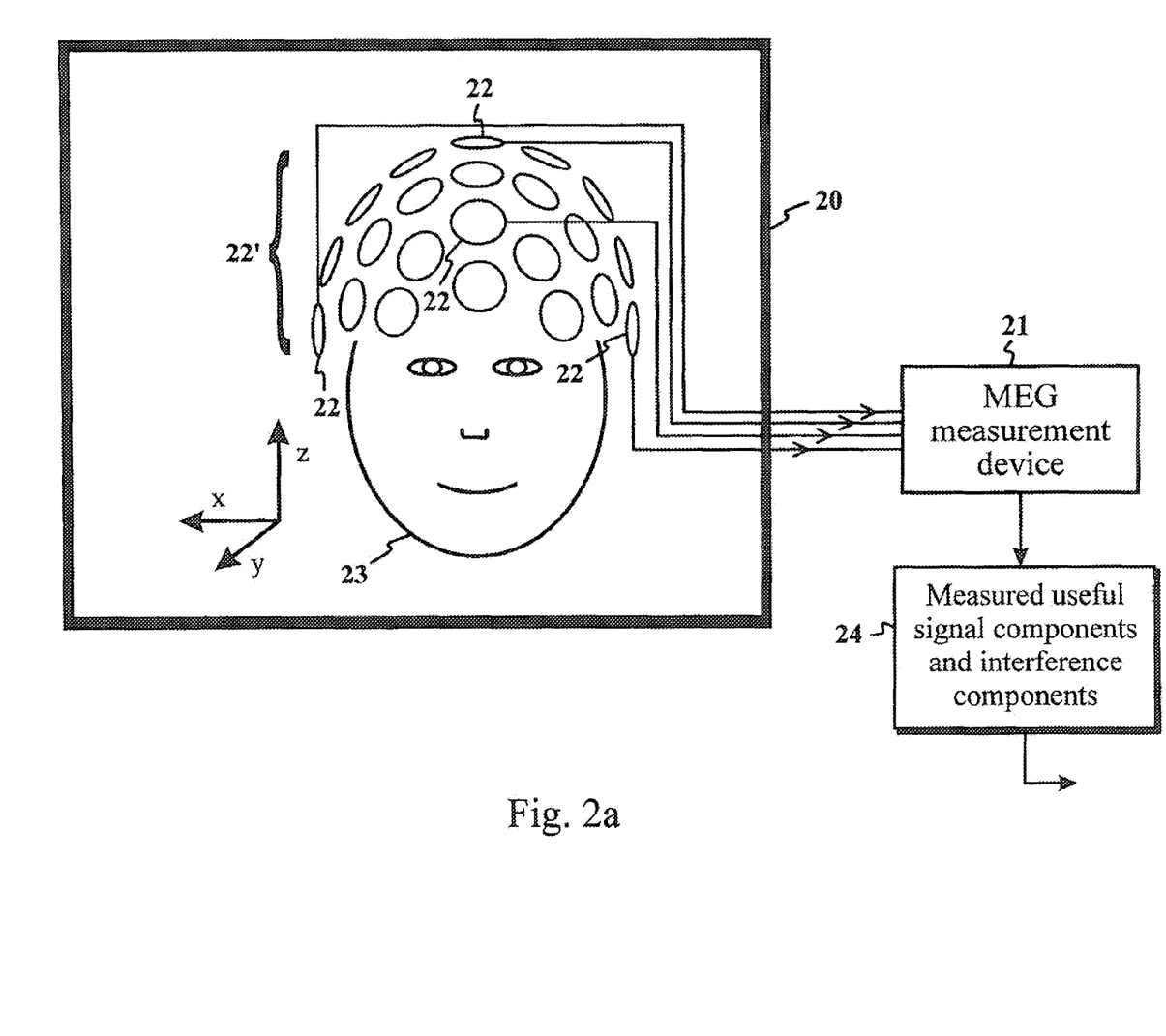
FIG. 2a shows an example of the measurement arrangement of a MEG apparatus, the object to be measured being present in the measurement situation.

FIG. 2a, in turn, shows an arrangement for MEG measurement in a situation where biomagnetic signals originating from the head 23 of a patient are normally measured. The actual MEG device 21 can be located outside a magnetically shielded room 20 in such a way that the sensors 22 acting as measurement channels are disposed as a helmet-shaped sensor assembly 22' inside the shielded room 20 and the connection from the sensors 22 to the measurement device 21 is led through the wall of the shielded room. In one embodiment of the invention, there are 306 sensors, i.e. measurement channels. Naturally, it is possible also to use another number of measurement channels. The measurement is performed as presented above and a signal 24 representing the prevailing magnetic fields is obtained as a result. In this situation, the sensors 22 observe the interesting signals originating from the head of the patient, the possible interference sources in the head or other parts of the patient, such as the heart, and the other external interference sources. As a result, all measured useful signal components and all measured internal and external interference components are obtained 24.

Figure 2B:
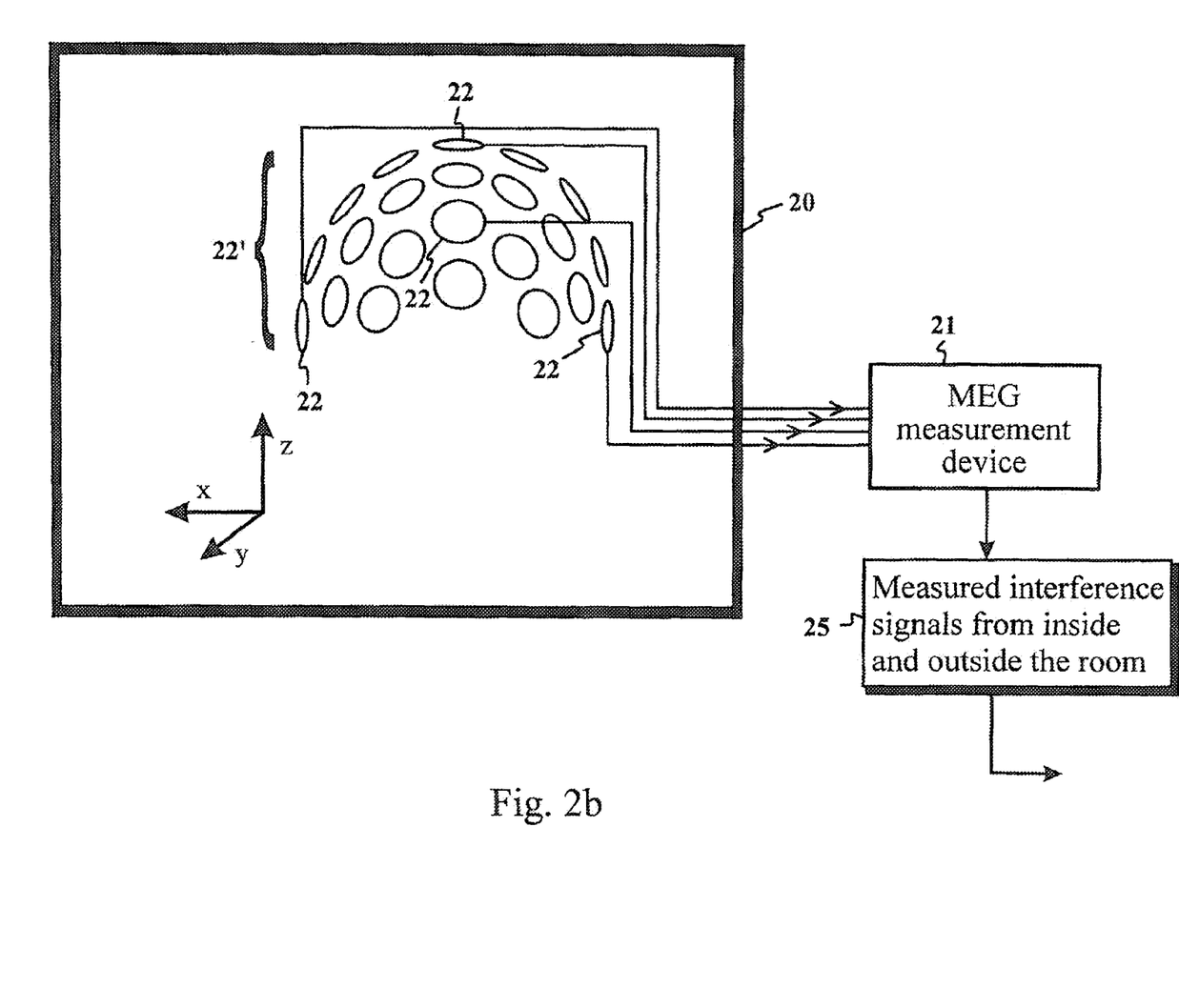
FIG. 2b shows an example of the measurement arrangement of a MEG apparatus, wherein only the sources considered as interferences are being measured.
Figure 2C:
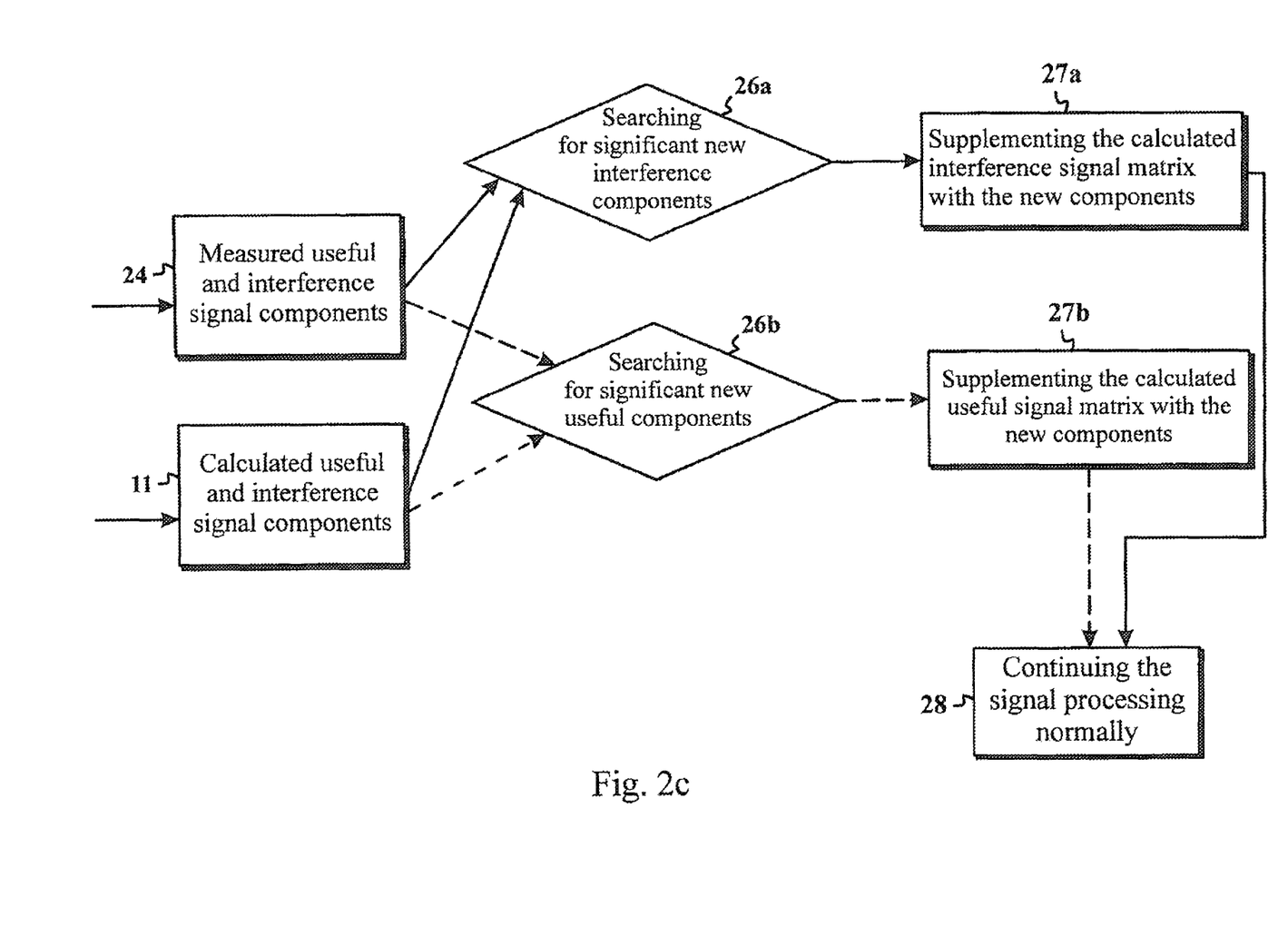
FIG. 2c shows an example for further processing of the results obtained from the measurements and calculation, FIG. 3a graphically shows a simplified example of the effect of the invention on the interference subspace to be processed in MEG measurements, and FIG. 3b graphically shows a simplified example of the effect of the invention on the useful signal subspace to be processed in MEG measurements.

FIG. 2b in turn shows a corresponding measurement situation in the so-called empty room case, i.e. without a separate object to be measured, or the patient. The measurement of empty room can be carried out before or after the actual MEG measurement of the patient, as long as care is taken that the other variables associated to the measurement arrangement remain as similar as possible between these measurements. The apparatus is thus the same as in FIG. 2a, including a sensor assembly 22' located in a magnetically shielded room 20 and a MEG device 21 performing data processing outside the shielded room. Via the measurement channels, the MEG device now produces the information about all prevailing interference signals 25 which may thus be caused by sources inside the shielded room (other than the patient under examination), the shielded room itself or interference sources originating from outside the room. The signal information obtained above can be expressed as sets of vectors, i.e. in a matrix form. FIG. 2c in turn shows one preferred principle of the further processing of the obtained sets of vector, i.e. matrices. In step 11 the calculated interference signal matrix having a size N*A, and in steps 24 or 25 the measurement-based interference signal matrix having a size N*B were determined. Next, the A calculated vectors are compared with the B measured vectors. From the B measured vectors, those significant components, i.e. mostly deviating from zero, which adjust the interference subspace already determined by the A vectors are picked 26a. This search of significant new interference components 26a also involves that the new interference components are linearly independent with the set of vectors A. If necessary, linearly dependent vectors are thus combined when the sum basis is being generated. As an end result 27a, a new matrix representing the adjusted interference space is thus obtained, having a size N*C, wherein A≤C≤A+B. This way, a set of interference signals 27a very accurately representing the real interferences has been obtained, and signal processing can now be continued in a desired manner 28.

FIG. 2c shows in broken line a possible second embodiment in the present invention, whereby the presented idea is also applied to the adjustment of the useful signal basis, i.e. the internal basis. In this case, the calculated subspace of the useful signals generated by the SSS method and the subspace of the useful signals obtained from the measurements are taken under examination. Since the calculated internal basis does not quite accurately correspond to the reality, components which are not yet present in the calculated basis are searched from the measured internal basis 26b. After this, the calculated basis obtained from the SSS can be supplemented with the new components 27b. At the same time, the redundant components are combined in such a way that the vectors in the sum basis are linearly independent of one another after the combination. Although the above-described adjustment of the interference basis to correspond more to the reality is practically more significant, the adjustment of the internal basis by this principle may also come into question. When the adjustments to the external and/or internal basis have been made 27ab, signal processing and analysis can be normally continued for example by means known from the SSS method 28.

Figure 3A:
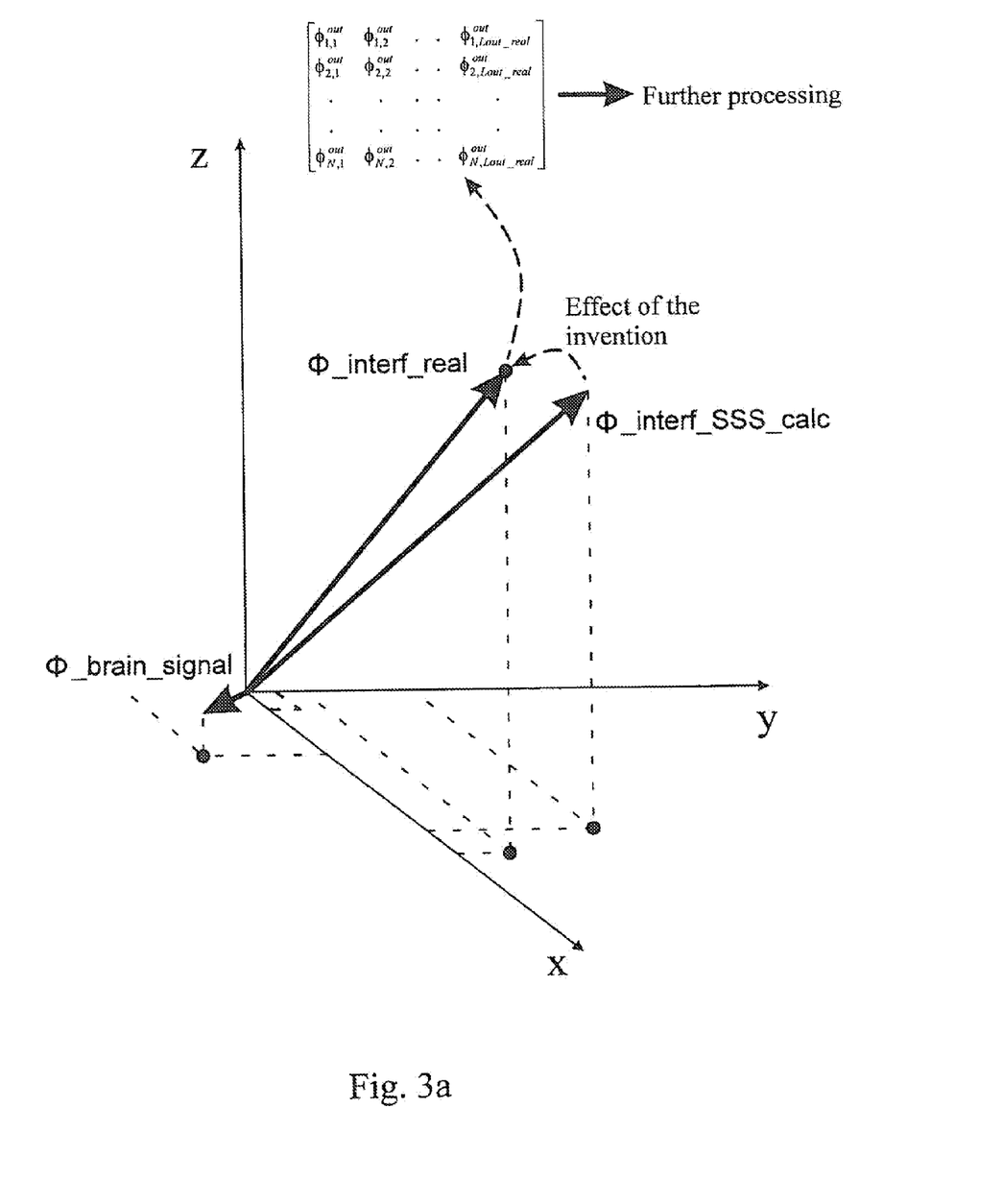
Figure 3B:
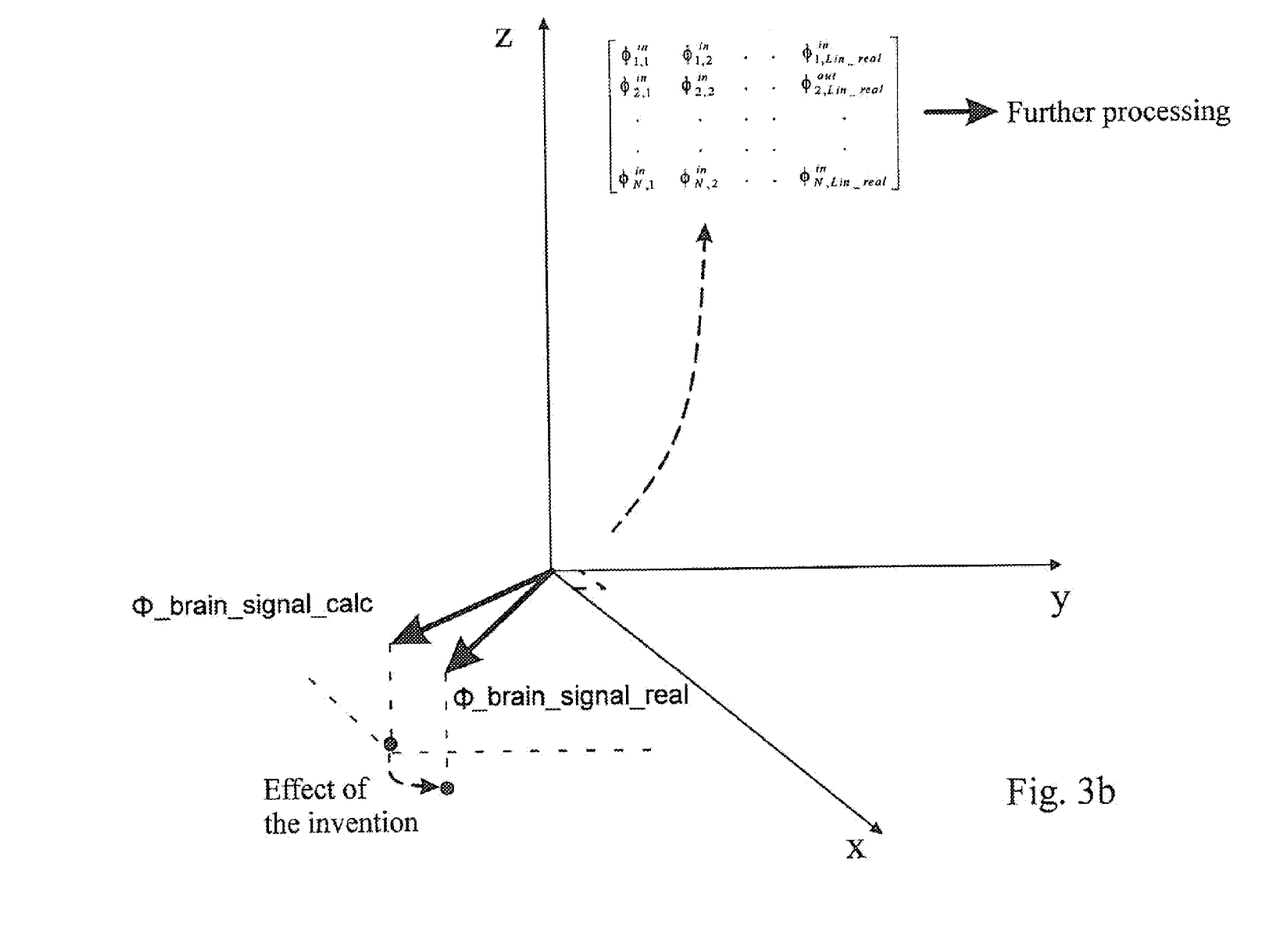

FIGS. 3a and 3b show the effect of the present invention on MEG measurement results by means of examples as illustrated with three-dimensional xyz coordinates. Although the vectors representing the measured signals are really N-dimensional (N being the number of the channels of the MEG device), the vectors in this example have been truncated to three-dimensional co-ordinates and vector points have further been projected to two-dimensional plane to improve clarity. When the measured signals have been processed in the above-described manner, a signal vector representing the useful brains signals can be determined, indicated in the figure as "Φ_brain_signal". Correspondingly, the calculated field portion caused by interference sources and separated by the SSS method is indicated as "Φ_interf_SSS_calc". The mutual amplitude ratios of the above-mentioned two signal points are only suggestive because the interference signals in the practical measurement situation may be several decades more intensive than the useful signals. The points at the bottom of the figure represent the projection points of the signal subspaces as projected to the xy-plane.

The effect of the invention on the signal subspaces can now be represented in a simplified manner by vector "Φ_interf_real". This new vector is represented in FIG. 2c by the process steps 26a and 27a. This vector represents the subspace of interferences adjusted by the invention, representing the actual situation much better than interference vector Φ_interf_SSS_calc. The effect of the present invention is thus that an adjustment, i.e. additional component, is calculated or determined for interferences for example by the measurement of empty room or by determining the poorly functioning channels, which vector is, algebraically expressed:

$$\Delta\Phi_{invention}=\Phi\_interf\_SSS\_calc-\Phi\_interf\_real \qquad (11)$$

This additional component is summed to the original calculated interference subspace vector, thereby obtaining an adjusted interference subspace:

$$\Phi_{real}^{interference} = \begin{bmatrix} \phi_{1,1}^{out} & \phi_{1,2}^{out} & \cdots & \cdots & \phi_{1,Lout\_real}^{out} \\ \phi_{2,1}^{out} & \phi_{2,2}^{out} & \cdots & \cdots & \phi_{2,Lout\_real}^{out} \\ \cdots & \cdots & \cdots & \cdots & \cdots \\ \cdots & \cdots & \cdots & \cdots & \cdots \\ \phi_{N,1}^{out} & \phi_{N,2}^{out} & \cdots & \cdots & \phi_{N,Lout\_real}^{out} \end{bmatrix} \qquad (12)$$

Finally, the desired further calculation is performed specifically using Φ_interf_real as the interference field vector. The "direction" of the added component may be basically any, i.e. the essential difference to the prior art projection methods is that any specific essential "direction" of interference, or the most significant interference component, is not taken away from the measured overall signal, but the amplitude and direction of the entire interference space is changed on the basis of a real measurement, i.e. for example the measurement of empty room.

FIG. 3b in turn shows an implementation corresponding to the embodiment branch represented in broken line in FIG. 2c, illustrated with vectors. Now, the object of examination is the signal subspace formed by the internal basis, i.e. the useful signals. The measurement result from which the portion of the internal basis has been separated after the SSS operation is expressed in FIG. 3b by vector "Φ_brain_signal_calc". After this, the steps 26b to 26b of the above-described embodiment in FIG. 2c can be illustrated by a useful signal subspace changed in terms of amplitude and direction, expressed by a simplified vector "Φ_brain_signal_real". The situation of FIG. 3b only represents an individual period under examination, because in practice the situation is dynamically continuously changing. As an end result, an adjusted useful signal vector is thus obtained in this embodiment, indicated in the figure as:

$$\Phi_{real}^{brain} = \begin{bmatrix} \phi_{1,1}^{in} & \phi_{1,2}^{in} & \cdots & \cdots & \phi_{1,Lin\_real}^{in} \\ \phi_{2,1}^{in} & \phi_{2,2}^{in} & \cdots & \cdots & \phi_{2,Lin\_real}^{in} \\ \cdots & \cdots & \cdots & \cdots & \cdots \\ \cdots & \cdots & \cdots & \cdots & \cdots \\ \phi_{N,1}^{in} & \phi_{N,2}^{in} & \cdots & \cdots & \phi_{N,Lin\_real}^{in} \end{bmatrix} \quad (13)$$

The further processing for the modified useful and/or interference signal bases can be made after this in a desired manner, for example by processing further with the SSS method.

The steps of the method presented for the invention can be carried out in applicable parts as a computer program that can be run on the data processing logic of the MEG device, i.e. typically on the processor of the device. The device may include a memory or other storage medium wherein the computer program, the data input and other parameters required by the method and the results obtained from the measurements can be stored.

The invention is not limited merely to the exemplifying embodiments referred to above; instead, many variations are possible within the scope of the inventive idea defined by the claims.

The invention claimed is:

1. A method for adjusting field components included in a magnetic field measured by a multichannel measurement device, wherein the measurement device comprises a set of measurement sensors and a data processing logic, and wherein the method comprises:
    generating first and second calculated signal subspaces by a Signal Space Separation (SSS) method by using the data processing logic, wherein the first calculated signal subspace represents vectors of signal components in a linearly independent signal basis of a signal originating from an object to be measured, and the second calculated signal subspace represents vectors of signal components in a linearly independent signal basis of interference signals;
    measuring a multichannel magnetic field of the interference signals by the set of measurement sensors without a signal source of the signal originating from the object to be measured to obtain a measured interference subspace;
    determining by using the data processing logic the most intensive forms of the interference signals, which substantially deviate from zero and which are due to at least one of interferences and incorrectly functioning signal channels from the measured interference subspace;
    comparing by using the data processing logic the signal components of the second calculated signal subspace with signal components of the measured interference subspace and, based on the comparison, adjusting said second calculated signal subspace by using the data processing logic by adding the most intensive forms of the interference signals thereto; and
    determining the signal originating from the object to be measured by using the data processing logic from a multichannel magnetic field measured by the set of measurement sensors with a presence of the signal source of the signal originating from the object to be measured, by utilizing the SSS method with the adjusted second calculated signal subspace.

2. The method according to claim 1, wherein the method further comprises:
    including measured magnetic field components of the interference signals in the most intensive form of the interference signals only when signal intensity associated to vectors representing such components exceeds a desired threshold value.

3. The method according to claim 1, wherein the method further comprises:
    adding at least one of measured components of the measured interference subspace to components of the second calculated signal subspace;
    supplementing the second calculated signal subspace by adjusting said second calculated signal subspace by adding the most intensive forms of the interference signals thereto; and
    combining components of the supplemented second calculated signal subspace in such a way that components of the adjusted second calculated signal subspace being generated form together a linearly independent basis.

4. The method according to claim 3, wherein the method further comprises:
    making the combination by calculating singular value decomposition for the components of the second calculated signal subspace under examination.

5. The method according to claim 1, wherein the method further comprises:
    dividing a signal of an incorrectly functioning signal channel in such a way as to include a correctly appearing signal component and an incorrect signal component; and
    including only the incorrect signal component from the incorrectly functioning signal channel in the measured interference subspace.

6. The method according to claim 5, wherein the method further comprises:
    respanning the first and second calculated signal subspaces after at least one incorrect signal component from the incorrectly functioning signal channel has been included in the measured interference subspace.

7. The method according to claim 1, wherein the method further comprises:
    determining an adjustment to the first calculated signal subspace generated on the basis of the performed magnetic field measurements in a manner corresponding to the second calculated signal subspace.

8. A multichannel measurement device arranged to measure a magnetic field and adjust the field components included therein, wherein the measurement device comprises:
    a set of measurement sensors; and
    a processor configured to:
        generate first and second calculated signal subspaces by a Signal Space Separation (SSS) method, wherein the first calculated signal subspace represents vectors of signal components in a linearly independent signal basis of a signal originating from an object to be measured, and the second calculated signal subspace represents vectors of signal components in a linearly independent signal basis of interference signals;

wherein the measurement device is further arranged to:

measure a multichannel magnetic field of the interference signals without a signal source of the signal originating from the object to be measured to obtain a measured interference subspace; and the processor is further configured to:

determine the most intensive forms of the interference signals, which substantially deviate from zero and which are due to at least one of interferences and incorrectly functioning signal channels from the measured interference subspace;

compare the signal components of the second calculated signal subspace with signal components of the measured interference subspace and, based on the comparison, adjust said second calculated signal subspace by adding the most intensive forms of the interference signals thereto; and determine the signal originating from the object to be measured from a multichannel magnetic field measured by the set of measurement sensors with a presence of the signal source of the signal originating from the object to be measured, by utilizing the SSS method with the adjusted second calculated signal subspace.

9. The measurement device according to claim 8, wherein the processor of the measurement device is further configured to:

include measured magnetic field components of the interference signals in the most intensive forms of the interference signals only when signal intensity associated to vectors representing such components exceeds a desired threshold value.

10. The measurement device according to claim 8, wherein the processor of the measurement device is further configured to:

add at least one of measured components of the measured interference subspace to components of the second calculated signal subspace;

supplement the second calculated signal subspace by adjusting said second calculated signal subspace by adding the most intensive forms of the interference signals thereto; and combine components of the supplemented second calculated signal subspace in such a way that components of the adjusted second calculated signal subspace being generated form together a linearly independent basis.

11. The measurement device according to claim 10, wherein the processor of the measurement device is further configured to:

make the combination by calculating singular value decomposition for the components of the second calculated signal subspace under examination.

12. The measurement device according to claim 8, wherein the processor of the measurement device is further configured to:

divide a signal of an incorrectly functioning signal channel in such a way as to include a correctly appearing signal component and an incorrect signal component; and include only the incorrect signal component from the incorrectly functioning signal channel in the measured interference subspace.

13. The measurement device according to claim 12, wherein the processor of the measurement device is further configured to:

respan the first and second calculated signal subspaces after at least one incorrect signal component from the incorrectly functioning signal channel has been included in the measured interference subspace.

14. The measurement device according to claim 8, wherein the processor of the measurement device is further configured to:

determine an adjustment to the first calculated signal subspace generated on the basis of the performed magnetic field measurements in a manner corresponding to the second calculated signal subspace.

15. A non-transitory computer readable medium storing a computer program for adjusting field components included in a magnetic field measured by a multichannel measurement device, wherein the measurement device comprises a set of measurement sensors and a data processing logic, and wherein the computer program comprises program code which, when run on the data processing logic, is arranged to execute:

generating first and second calculated signal subspaces by a Signal Space Separation (SSS) method, wherein the first calculated signal subspace represents vectors of signal components in a linearly independent signal basis of a signal originating from an object to be measured, and the second calculated signal subspace represents vectors of signal components in a linearly independent signal basis of interference signals;

wherein the computer program is further arranged to execute:

measuring a multichannel magnetic field of the interference signals without a signal source of the signal originating from the object to be measured to obtain a measured interference subspace;

determining the most intensive forms of the interference signals, which substantially deviate from zero and which are due to at least one of interferences and incorrectly functioning signal channels from the measured interference subspace;

comparing the signal components of the second calculated signal subspace with signal components of the measured interference subspace and, based on the comparison, adjusting said second calculated signal subspace by adding the most intensive forms of the interference signals thereto; and determining the signal originating from the object to be measured from a multichannel magnetic field measured by the set of measurement sensors with a presence of the signal source of the signal originating from the object to be measured, by utilizing the SSS method with the adjusted second calculated signal subspace.

* * * * *